United States Patent

Pretlow, III

Patent Number: 5,782,767
Date of Patent: Jul. 21, 1998

[54] COUPLING PAD FOR USE WITH MEDICAL ULTRASOUND DEVICES

[75] Inventor: Robert A. Pretlow, III, Kirkland, Wash.

[73] Assignee: Diagnostic Ultrasound Corporation, Redmond, Wash.

[21] Appl. No.: 777,581

[22] Filed: Dec. 31, 1996

[51] Int. Cl.⁶ .................................................. A61B 8/00
[52] U.S. Cl. ............................................................ 600/443
[58] Field of Search .............................. 128/662.03, 660, 128/661.07

[56] References Cited

U.S. PATENT DOCUMENTS

| | | | |
|---|---|---|---|
| 4,556,066 | 12/1985 | Semrow | 128/660 |
| 5,078,149 | 1/1992 | Katsumata et al. | 128/662.03 |
| 5,265,614 | 11/1993 | Hayakawa et al. | 128/662.03 |
| 5,575,291 | 11/1996 | Hayakawa et al. | 128/662.03 |

Primary Examiner—Marvin M. Lateef
Assistant Examiner—Maulin Patel
Attorney, Agent, or Firm—Jensen & Puntigam, P.S.

[57] ABSTRACT

A pad assembly for coupling ultrasound from a transducer probe into the human body includes a shallow receptacle 20 with a removable cover 22 on the upper portion thereof. Within the receptacle are a foam section 14, a gel pad 12 and a thin net section 18. The net section 18 is bonded to the cover 22. The gel pad 12 is impregnated with a mixture of glycerin and water. The upper surface of foam section 14 is convoluted or ribbed so that there is a substantially lower surface tension between the foam section 14 and the gel pad than between the probe and the gel pad. There is also a substantially lower surface tension between net section 18 and the gel pad than between the gel pad and the foam section.

12 Claims, 2 Drawing Sheets

5,782,767

COUPLING PAD FOR USE WITH MEDICAL ULTRASOUND DEVICES

TECHNICAL FIELD

This invention relates generally to ultrasound medical devices, and more specifically concerns a coupling member for coupling ultrasound signals between an ultrasound transmitter/receiver probe or head and the skin of the patient.

BACKGROUND OF THE INVENTION

Medical ultrasound scanning devices generate and transmit sound energy, typically in a frequency range of 2–10 megahertz, into the human body and then detect the returning echo signals from the body. Since the medium of air significantly attenuates the ultrasound frequencies used in medical applications, a coupling medium, typically a gel material, is used between the surface of the ultrasound probe and the skin of the patient, in order to displace the air therebetween. Such gels, however, which are liquid or semi-liquid, are inconvenient to use and have several other disadvantages. They are cold and unpleasant to the patient, they often result in wetting the patient's clothing, and they typically require a substantial amount of time for the ultrasound technician to clean up. It would be desirable to have a coupling medium or member which is easier to use and more convenient than such a gel.

DISCLOSURE OF THE INVENTION

Accordingly, the present invention is a pad assembly which includes a member for coupling ultrasound signals from an ultrasound probe into the human body, comprising: a pad adapted for coupling of ultrasound signals between an ultrasound probe and a human body; a support member on which said pad is positioned, wherein the support member is characterized by an upper surface which is configured and arranged to have a lower surface tension between it and the pad than that between the ultrasound probe and the pad, so that when the probe is pressed against the pad and then lifted, the pad remains with the probe, wherein the probe can then be positioned adjacent the desired skin area of the body, the pad being between the probe and the desired skin area; and a receptacle for the pad and the support member.

BEST MODE FOR CARRYING OUT THE INVENTION

Figure 1:
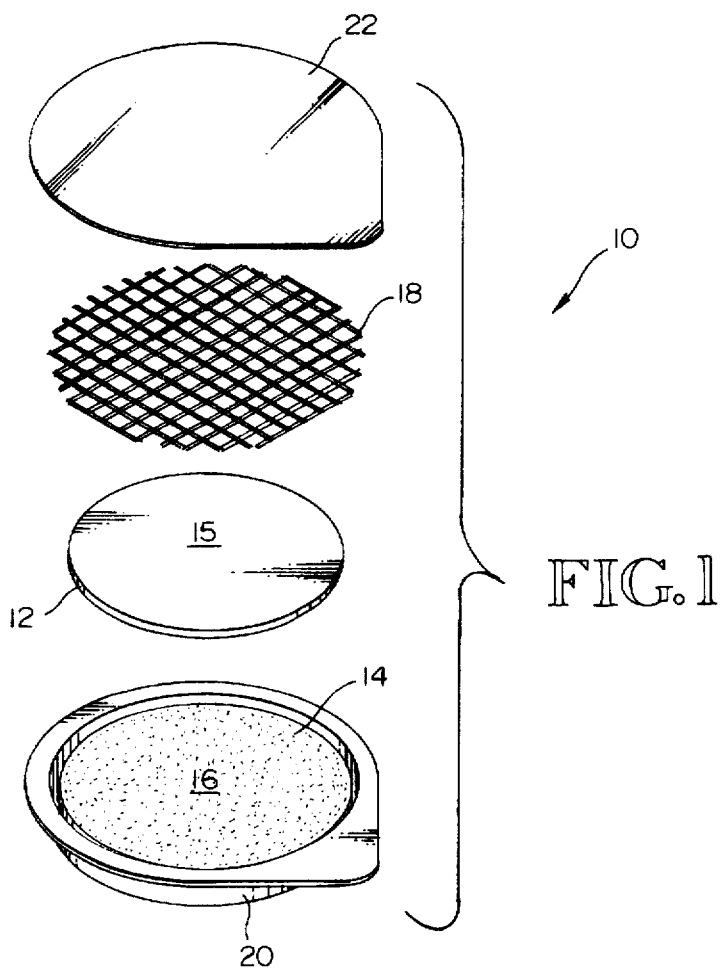
FIG. 1 is an exploded view of the gel pad assembly of the present invention.

FIG. 1 shows the gel pad assembly 10 of the present invention. The gel pad assembly includes a relatively thin (approximately 0.06 inches) gel pad 12 which in use is positioned between an ultrasound transducer probe and a selected skin area of a patient. In the embodiment shown, gel pad 12 is circular, approximately 2.5 inches in diameter, and is made from cellulose or equivalent material, typically impregnated with a mixture of glycerin and water, or other liquid suitable for ultrasound coupling, such as certain oils, including generally water-soluble glycols, such that the opposed surfaces of the pad are pliable, wet and slippery, and will displace any air between the pad and the skin surface and between the pad and the probe surface. The term gel pad is used herein as a descriptive, inclusive term to mean a pad having the above described characteristics, displacing air as indicated, even though "gel" per se may not be used in the pad.

Gel pad 12 is an effective coupling medium between an ultrasound transducer probe and the body of the patient, preventing signal attenuation which would occur in the absence of such a coupling member. Gel pad 12 could comprise multiple layers, with the outer layers having the above-described characteristics which displace air from between the pad and the probe and the patient's skin, respectively.

As explained above, in present practice, a given amount of a conventional liquid or semi-liquid ultrasound gel is placed either on the transducer probe, the desired skin area of the patient and/or both. The probe is then positioned on the desired skin area, directly on the gel, and the ultrasound procedure is then begun. The present invention replaces the conventional use of the ultrasound gel. The ultrasound probe used with the present invention and discussed herein may have various configurations, but generally refers to the transducer/receiver member which is connected to an ultrasound generating device for transmitting ultrasound signals into a desired area of the body and to receive returning signals therefrom. It should be understood that the ultrasound probe per se is not a part of the present invention.

Ultrasound is currently used for a wide variety of diagnostic and monitoring purposes, including, for example, monitoring the development of a fetus within the womb and investigating the condition of various areas of the heart and/or the arterial system supplying blood to the heart. There are numerous other applications for ultrasound in the medical field.

Gel pad assembly 10 further includes a circular section of foam 14. In the embodiment shown, the foam section 14 is approximately 2.5 inches in diameter (approximately the same diameter as gel pad 12) and 0.135 inches thick. Upper surface 16 of foam section 14 is either open cell (with a relatively large cell size, typically 0.020 inches in diameter) or is convoluted or ribbed. The convolutions may take various configurations; the intent is to create a rather low surface tension between upper surface 16 of foam section 14 and the adjacent surface of gel pad 12. Gel pad 12 rests on the upper surface of foam section 14 in the gel pad assembly but is not otherwise secured thereto.

Resting against upper surface 15 of gel pad 12 is a thin plastic net section 18, which has the same diameter and configuration as gel pad 12 and foam section 14, but in the embodiment shown is considerably thinner than foam section 14, approximately 0.03 inches. Net section 18 is typically made of polypropylene or any other thin plastic material with a weave opening size approximately 0.125 inches in diameter. Basically, the purpose of the plastic net section 18 is to prevent gel pad 12 from adhering to a cover 22 of the assembly. Net section 18 presents a surface tension to the gel pad that is lower than that presented by the foam section 14, so the gel pad will remain on foam section 14 when cover 22 is removed. The net section 18 is adhesively bonded to cover 22.

The three elements 12, 14 and 18 discussed above are positioned in a receptacle which includes a lower cup portion 20 and cover portion 22. Cup portion 20 is shallow, approximately 0.25 inches high, and has an internal diameter which is large enough to accommodate gel pad 12, foam section 14 and net section 18. Cup portion 20 in the embodiment shown is made of thin plastic, such as polyester. Cover portion 22 overlays net section 18, with net section 18 being bonded to the cover portion; cover portion 22 is secured around the periphery thereof to the upper edge of cup portion 20, typically by means of an adhesive.

Figure 4:
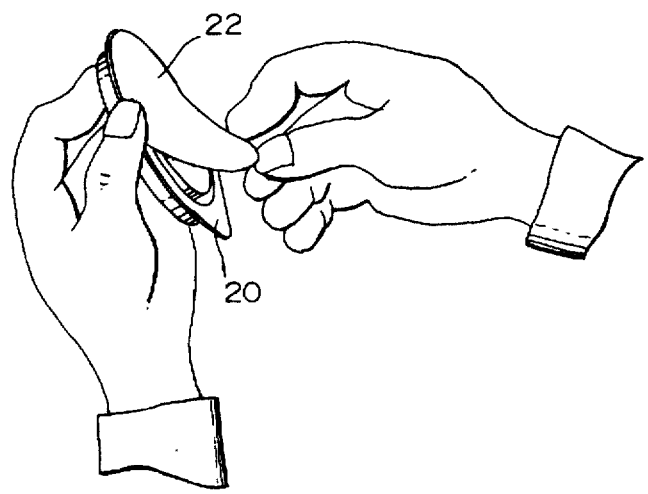
FIG. 4 is a schematic view of a first step in the use of the gel pad assembly of FIG. 1.

In use of gel pad 12, cover portion 22 is first removed from cup portion 20, simultaneously removing net section 18, as shown in FIG. 4. The attachment and removal of cover 22 can be accomplished in a number of ways. If an adhesive is used, typically the entire cover will be pulled away by the user. Gel pad 12 is now exposed.

Figure 5:
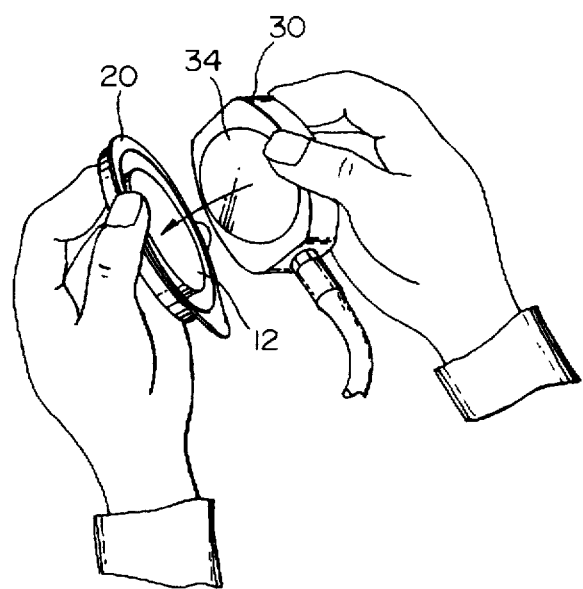
FIG. 5 is a schematic view showing a second step in the use of the gel pad assembly of FIG. 1.

At this point, the ultrasound transducer probe 30 is brought into contact against the upper surface of the exposed gel pad 12, as shown in FIG. 5 and the arrow therein. A cord provides a signal connection between transducer probe 30 and the ultrasound generating and processing apparatus. The ultrasound probe 30 will typically include a curved or partially domed portion 34.

Figure 2:
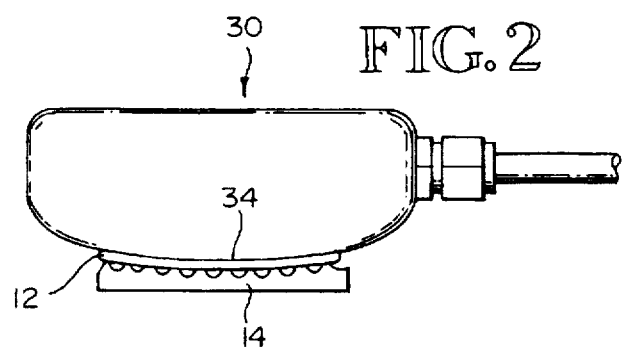
FIG. 2 is a cross-sectional view of the gel pad of FIG. 1 as an ultrasound probe is initially brought into contact therewith.

Domed portion 34 is adapted to be placed on the desired skin area of the patient. Typically, domed portion 34 is quite smooth so that it has a relatively high surface tension when it contacts the gel pad; in particular, the surface tension is much greater than that of the upper surface of foam section 14. Domed portion 34 is pressed against the upper surface of gel pad 12. The physical relationship between domed portion 34 of probe 30, gel pad 12 and foam section 14 at this point is shown most clearly in FIG. 2.

Figure 6:
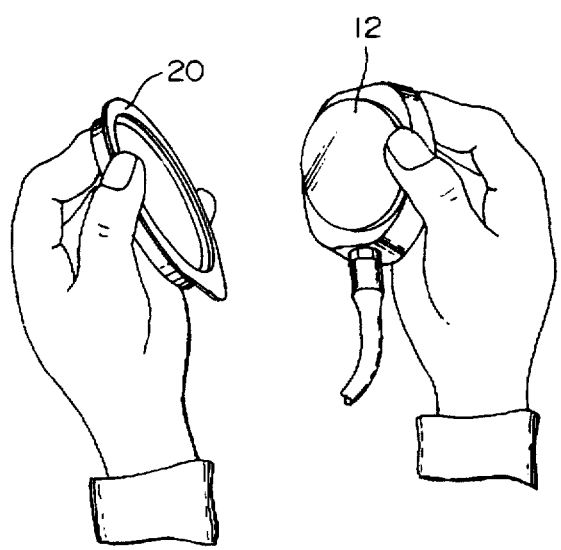
FIG. 6 is a schematic view showing the third step in the use of the gel pad assembly of FIG. 1.

In the next step, as shown in FIG. 6, probe 30 is lifted away from the gel pad assembly. However, because the surface tension between gel pad 12 and domed portion 34 is significantly higher than the surface tension between the gel pad and the foam section, gel pad 12 remains fixed to domed portion 34 as the probe is moved away. Hence, gel pad 12 remains positioned firmly on the domed portion of the probe without the operator having to come into contact with the gel pad itself or any of the glycerin thereon.

Figure 3:
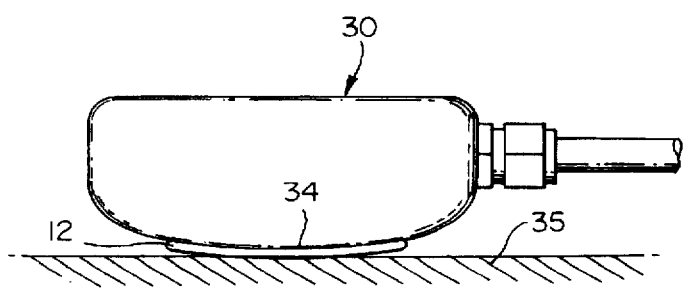
FIG. 3 is a cross-sectional view showing an ultrasound probe with the gel pad of FIG. 1 positioned on a skin portion of a patient.

In the next step, the ultrasound probe with the gel pad thereon is positioned on the desired skin area of the patient. The gel pad lies against the skin and provides an effective coupling medium between ultrasound probe 30 and the patient's body. Because the gel pad is pliable, slippery and wet, it displaces any air between the pad and the skin of the patient, including any skin irregularities caused by hair, as well as any air between the pad and the surface of the probe. The relationship is illustrated in FIG. 3, showing probe 30, gel pad 12 which is positioned on the domed portion 34 of the probe, and the skin area 35 of the patient.

At this point, operation of the ultrasound device can begin, with ultrasound signals being generated and transmitted into the body of the patient through the gel pad coupling element; the returning echo signals from the body are also received through the gel pad. When the procedure is completed, the ultrasound probe along with the gel pad is ultrasound removed from the patient's body. Because the surface tension between the probe and the gel pad is higher than that between the gel pad and the skin, the gel pad remains in place on the probe when the probe is removed from the skin. Any residual glycerin/water mixture from the gel pad, which is typically minimal, left on the skin of the patient is either left there to be absorbed into the skin or quickly (and conveniently) wiped clean.

Any residual glycerin/water mixture on the domed portion 34 is also wiped away. Foam section 14 which remains in cup portion 20 and cup portion 20 itself may be discarded or may be used to remove the gel pad from the probe. By pressing the probe with the gel pad in place back on the foam section 14 and sliding the probe and the gel pad laterally against the lip of cup portion 20, the gel pad can be removed from the probe without the operator having to come into contact with the gel pad. The used gel pad 12, cup portion 20 and foam section 14 can then all be discarded.

Hence, a gel pad assembly has been disclosed which provides a convenient and effective coupling medium between the ultrasound probe and the skin without the disadvantages of conventional liquid or semi-liquid gel.

Although a preferred embodiment of the invention has been disclosed herein for illustration, it should be understood that various changes, modifications and substitutions may be incorporated in such embodiment without departing from the spirit of the invention, which is defined by the claims as follows:

I claim:

1. An ultrasound coupling assembly, comprising:
   a thin pad adapted for coupling of ultrasound signals between an ultrasound probe and a human body;
   a support member on which said pad is positioned prior to use, wherein the support member includes an upper surface which is configured and arranged to have a surface tension which is lower between it and the pad than that between the ultrasound probe and the pad, so that when the probe is pressed against the pad and then lifted, the pad remains with the probe, wherein the probe can then be positioned adjacent a desired skin area of the body, the pad being between the probe and the desired skin area; and
   a receptacle for the pad and the support member.

2. The assembly of claim 1, wherein the pad is pliable.

3. The assembly of claim 1, wherein the support member is foam and the upper surface thereof is convoluted.

4. The assembly of claim 2, wherein the pad is impregnated with an ultrasound conducting liquid, the liquid acting to displace air between the pad and the probe, as well as between the pad and the desired skin area when the probe and the pad are operatively positioned on the desired skin area.

5. An article of claim 1, wherein the support member is a large open cell foam material.

6. An article of claim 1, including a removable cover portion which extends over and covers the pad and the support member and is secured to an upper edge of the receptacle.

7. An article of claim 6, including a thin net member positioned between the pad and the cover portion, wherein the net member is attached to the cover portion and wherein the surface tension between the net member and the pad is less than that between the pad and the support member, so that when the cover portion is removed, the pad remains on the support member.

8. An article of claim 1, wherein the surface tension between the pad and the probe is greater than the surface tension between the pad and the desired skin area of the body, so that as the probe is moved away from the body, the pad remains with the probe.

9. The assembly of claim 7, wherein the pad, the support member and the net member have approximately the same outline.

10. A pad for use with an ultrasound probe for coupling ultrasound signals into a human body, comprising:

a pad member, impregnated with an ultrasound conducting liquid, capable of conducting ultrasound signals from a probe source thereof into a skin area of the human body, the pad being pliable and wet at its respective opposed surfaces so that any air between the pad and, respectively, the probe and the skin area is displaced when the pad is positioned between the probe and the skin area.

11. The pad of claim 10, wherein the pad material is cellulosic material.

12. The pad of claim 10, wherein the liquid is a combination of water and glycerin.

* * * * *